United States Patent [19]

Jacobs

[11] 4,416,734
[45] Nov. 22, 1983

[54] SEPARATION OF NITROALKANOL BY AZEOTROPIC DISTILLATION

[75] Inventor: Martin J. Jacobs, Terre Haute, Ind.

[73] Assignee: Angus Chemical Company, Northbrook, Ill.

[21] Appl. No.: 262,078

[22] Filed: May 11, 1981

[51] Int. Cl.³ .......................... B01D 3/36; C07C 79/18
[52] U.S. Cl. ........................................ 203/18; 203/48; 203/56; 203/60; 203/62; 203/63; 203/69; 203/70; 568/704; 568/712
[58] Field of Search ................ 568/712, 704; 203/48, 203/50–70, 14–17, 18, 19

[56] References Cited

U.S. PATENT DOCUMENTS

| | | | |
|---|---|---|---|
| 2,301,259 | 11/1942 | Cox | 568/712 |
| 2,327,961 | 8/1943 | Degering et al. | 568/712 |
| 2,347,312 | 4/1944 | Cox | 568/712 |
| 2,441,602 | 5/1948 | Snow et al. | 203/48 |
| 2,474,735 | 6/1949 | Harmon | 203/48 |
| 2,480,380 | 8/1949 | Nicholl et al. | 203/48 |
| 2,602,045 | 7/1952 | Hodge | 203/48 |
| 2,831,900 | 4/1958 | Ferentchak et al. | 203/55 |
| 3,081,349 | 3/1963 | Spacht | 203/48 |
| 3,231,605 | 1/1966 | Blumbergs | 203/48 |
| 3,269,923 | 8/1966 | Roche et al. | 203/48 |
| 3,472,929 | 10/1969 | Jones et al. | 203/14 |
| 3,624,174 | 11/1971 | Sugerman | 203/48 |
| 3,647,639 | 3/1972 | Buls et al. | 203/14 |
| 4,026,681 | 5/1977 | Roskelley | 203/48 |

OTHER PUBLICATIONS

Horsley: Azeotropic Data-III 1973 (pp. 468 & 469).
Perry et al.: Technique of Organic Chemistry IV-Distillation 1965 pp. (506 & 507).

*Primary Examiner*—Wilbur L. Bascomb, Jr.
*Attorney, Agent, or Firm*—Leydig, Voit, Osann, Mayer & Holt, Ltd.

[57] ABSTRACT

A process for the separation of a dissolved solid from an aqueous solution containing it, comprising the steps of (a) adding thereto an organic liquid which is a poor solvent for the dissolved solid and which forms an azeotrope with water, (b) subjecting the mixture to azeotropic distillation to separate at least a major portion of the water, (c) cooling the mixture thereby causing substantially complete separation of the dissolved solids, and (d) separating same from the mother liquor.

23 Claims, No Drawings

SEPARATION OF NITROALKANOL BY AZEOTROPIC DISTILLATION

BACKGROUND OF THE INVENTION

This invention relates to a method for recovery of a dissolved solid from a solution containing it.

In a particular aspect, this invention relates to a method for recovering crystalline nitroalkanol from a solution containing it.

Nitroalkanols, including the diols and the triols, are readily prepared by condensing a nitroalkane with an aldehyde in the presence of an alkaline catalyst, as is known. The reaction is usually conducted in an aqueous medium and the product is obtained as an aqueous solution of the nitroalkanol. It is recovered by concentrating and cooling the aqueous solution to crystallize the nitroalkanol.

Four nitroalkanes of from 1 to 3 carbon atoms are commercially available and from these, five nitroalkanols are commercially available, obtained by condensing the nitroalkane with one or more moles of formaldehyde. Of these five compounds, four are crystalline solids and one, 2-nitro-1-butanol, is a liquid. The solid compounds do not liquify at elevated temperatures but rather melt with decomposition.

The commercial crystalline nitroalkanols are highly soluble in water. For example, following are their solubilities at 20° C. in 100 g of water.

| | |
|---|---|
| 2-Nitro-2-methyl-1-propanol | 350 g |
| 2-Nitro-2-methyl-1,3-propanediol | 80 g |
| 2-Nitro-2-ethyl-1,3-propanediol | 400 g |
| Tris(hydroxymethyl)nitromethane | 200 g |

Previously these compounds have been commercially prepared by crystallizing them from aqueous solution. However, due to the high solubility in water, the yields are poor and a significant waste disposal problem exists. R. F. Cox, U.S. Pat. No. 2,347,312, disclosed a process which gave improved yields of crystalline tris(hydroxymethyl)nitromethane, hereinafter designated TN, by condensing nitromethane and formaldehyde in the presence of an organic solvent so that the TN remained in solution at the reaction temperature, but crystallized when chilled. The solvents employed included lower aliphatic alcohols but such mixtures as ethyl acetate with hexane and butyl alcohol with toluene were suggested.

This process suffered from two disadvantages. The principal one was that the reaction was much slower in organic solvent than in aqueous solution and the solubility even when chilled was still significant. Consequently, the problems of low yield and disposal of wastes continued. Furthermore, the longer reaction time lowered the productivity and raised the energy requirements. Accordingly, there is a need for an improved method recovering these highly soluble compounds from solutions containing them.

SUMMARY OF THE INVENTION

It is an object of this invention to provide a method for the recovery of a dissolved solid from solution.

It is another object of this invention to provide a method for the production of a nitroalkanol from a solution containing it.

Other objects of this invention will be apparent to those skilled in the art from the disclosure herein.

It is the discovery of this invention to provide a process for the separation of dissolved solids from an aqueous solution thereof comprising the steps of (a) adding to the solution an organic liquid which is a poor solvent for the dissolved solid and which forms an azeotrope with water, (b) subjecting the mixture to azeotropic distillation to separate at least a major portion of the water, (c) cooling the mixture, thereby causing substantially complete separation of the dissolved solids and (d) separating same from the mother liquor.

DETAILED DESCRIPTION

It is contemplated that the process of this invention will be of value for any solid which is soluble in water but which is relatively poorly soluble in an organic liquid which forms an azeotropic mixture with water. However, in the description herein, the process will be exemplified as it applies to nitroalkanols and especially to tris(hydroxymethyl)nitromethane (TN).

According to the process of this invention, water is conveniently and economically removed from an aqueous solution as an azeotrope with the organic liquid. If an excess of organic liquid is present, a dissolved solid in the aqueous phase, such as a nitroalkanol, separates as the water is removed, especially so after cooling. In the present invention, impurities in the aqueous solution are soluble in the organic liquid so that when the nitroalkanol crystallizes and is separated from the mother liquor, the impurities are substantially separated along with the mother liquor.

The nitrohydroxy compounds which can be advantageously and economically crystallized by the process of this invention include 2-nitro-2-methyl-1-propanol; 2-nitro-2-methyl-1,3-propanediol; 2-nitro-2-ethyl-1,3-propanediol and tris(hydroxymethyl)nitromethane. The method is particularly useful for the latter compound because of its very high water solubility (about 400 g per 100 ml) and low solubility in organic liquids.

The preferred organic liquids useful in the practice of this invention are mixtures which form ternary azeotropes with water. Such mixtures include but are not limited to mixtures of alkanols of 2-4 carbon atoms with alkanes of 6-9 carbon atoms, benzene or toluene. Also included are mixtures of alkanols with ketones, esters and butyl ether. Such mixtures are known to form ternary azeotropes as set forth in the following table.

| A-Component Water | B-Component | C-Component | % | Azeotrope B.P. °C. |
|---|---|---|---|---|
| | Ethanol | | | |
| 7.4% | 18.5% | Benzene | 74.1 | 64.86 |
| 3 | 18.7 | Hexane | 78.3 | 56.4 |
| 3 | 12 | Hexane | 85 | 56.0 |
| 6.1 | 33.0 | Heptane | 60.9 | 68.8 |
| 11 | 14 | 2-Butanone | 75 | 73.2 |
| 12 | 37 | Toluene | 51 | 74.4 |
| | 2-Propanol | | | |
| 7.5% | 18.7% | Benzene | 73.8 | 66.5 |
| 7.5 | 18.5 | c-Hexane | 74 | 64.3 |
| 8.2 | 19.8 | Benzene | 72.0 | 65.7 |
| 13.1 | 38.2 | Toluene | 48.7 | 76.3 |
| | n-Propanol | | | |
| 8.6% | 9.0% | Benzene | 82.4 | 68.5 |

-continued

| A-Component Water | B-Component | C-Component, % | | Azeotrope B.P. °C. |
|---|---|---|---|---|
| 8.5 | 10.0 | c-Hexane | 81.5 | 66.5 |
| 17 | 10 | n-Propyl Acetate | 73 | 82.5 |
| 27 | 63 | 2-Hexanone | 10 | 87.0 |
| n-Butanol | | | | |
| 19.2% | 2.9% | Hexane | 77.9 | 61.5 |
| 41.4 | 7.6 | Heptane | 51 | 78.1 |
| 60 | 14.6 | Octane | 25.4 | 86.1 |
| 69.9 | 18.3 | Nonane | 11.8 | 90 |
| 21.3 | 10 | n-Butyl Formate | 68.7 | 83.6 |
| 37.3 | 27.4 | n-Butyl Acetate | 35.3 | 89.4 |
| 29.3 | 42.9 | Butyl Ether | 27.7 | 90.0 |
| sec-Butanol | | | | |
| 7% | 5% | Benzene | 88 | 80.1 |
| 10.9 | 22.2 | Heptane | 66.9 | 75.8 |
| 10.6 | 21.9 | i-Octane | 67.5 | 76.3 |
| 20.2 | 27.4 | sec-Butyl Acetate | 52.4 | 85.5 |
| tert-Butanol | | | | |
| 8.1% | 21.4% | Benzene | 70.5 | 67.3 |
| 8 | 21 | c-Hexane | 71 | 65 |
| iso-Butanol | | | | |
| 30.4% | 23.1% | iso-Butyl Acetate | 46.5 | 86.8 |
| 17.3 | 6.7 | iso-Butyl Formate | 76 | 80.2 |

The preferred liquid mixtures are those which remove the maximum amount of water. Thus 2-component mixtures of n-butanol with nonane, octane, heptane, n-butyl acetate, butyl ether and isobutanol with isobutyl acetate are particularly preferred.

In the practice of this invention, the approximate water content of the nitroalkanol solution is determined by any convenient method, many of which are known. Components B and C are then selected and the amount of Component C needed to remove the water is then calculated, using the data in the foregoing table. The minimum amount of Component B is then calculated. These amounts of B and C can be premixed and added to the nitroalkanol solution, or they can be added separately. Preferably in excess of B, or optionally an excess of a mixture of B and C, is added inasmuch as it is not intended to evaporate to dryness. Rather it is intended that a considerable amount of liquid remain after the ternary azeotrope is removed to maintain in solution the impurities and by-products of the reaction. For example, the amount of excess B (or mixture of B and C), can be equal to the initial water content. It is well within the skill of the ordinary artisan to select the B and C components and the optimum amounts of each.

The above mixture, which may be two-phase, now is subjected to azeotropic distillation at atmospheric or reduced pressure and the ternary azeotrope separated. Usually the azeotrope separates into two layers. The lower water layer is removed and the upper layer can, if desired, be returned to the distillation kettle. The water layer can be processed for recovery of dissolved B-component if desired.

When the water component has been separated, distillation is discontinued and the nitroalkanol mixture is cooled to room temperature, or preferably below, thereby causing nitroalkanol crystals to develop. These are then separated by any convenient method, such as filtration, centrifugation or decantation. The crystals may be used as is or they may be further rectified.

It is understood that the practice of this invention is not limited to the B- and C-components recited in the table. Rather, any pair of components which form ternary azeotropes with water may be used.

It is to be understood that it is not necessary to remove all of the water in order to obtain a suitable product. A suitable product can be obtained by conducting the azeotropic distillation just until crystals appear. Cooling the solution to room temperature or less then may provide a satisfactory yield of high quality crystals.

The invention will be better understood with reference to the following examples. It is understood that the examples are intended only to illustrate the invention, and it is not intended that the invention will be limited thereby.

EXAMPLE 1

An aqueous concentrate, 50%, of TN was made by a known process. Of this, 100 g was diluted with 400 ml of a 1:1 by volume mixture of n-butanol and hexane. The mixture was delivered to a distillation vessel and heated to remove the butanol-water-hexane azeotrope. The vapor temperature was 63° C. and the vessel temperature was 67° C. When 42 ml of the azeotrope had been collected, crystals began to form in the vessel. The reaction mixture was cooled to 20°–25° C. and the crystals were separated by centrifugation and washed with 10 ml of hexane. The product was air-dried overnight yielding 82% recovery of the TN. The product was odorless and had the same crystalline form as TN prepared by the known process. Following is a comparison of products prepared by the conventional process and the above (new) process. Although the product is less pure by the new process, it is suitable for most uses.

| | Conventional | New |
|---|---|---|
| Melting Point, °C. | 166.5 | 152.5 |
| Color of 20% Solution, Gardner | 1 | 2 |
| pH of 20% Solution | 6.64 | 5.32 |
| Water, % by weight | 0.17 | 0.17 |
| TN, % by weight | 98.9 ± 1.5 | 96.8 ± 1.5 |

EXAMPLE 2

The experiment of Example 1 is repeated in all essential details except that heptane is substituted for hexane. A high yield of good quality crystals is obtained.

EXAMPLE 3

The experiment of Example 1 is repeated in all essential details except that octane is substituted for hexane. A high yield of good quality crystals is obtained.

EXAMPLE 4

An aqueous solution of 2-nitro-2-ethylpropanediol (NEPD) is analyzed and determined to contain 25% water. A 100 g portion, containing 25 g water, is delivered to a distillation flask. n-Butanol and nonane are selected as the B- and C-components, respectively. Approximately 12 g of nonane and 18 g of n-butanol will form an azeotrope with 70 g of water. It is calculated that the minimum amounts of nonane and butanol required are 4.28 g and 6.4 respectively. However, it is desired to have a considerable excess of liquid remaining after the distillation, so a mixture containing 5 g of nonane and 100 g of butanol is added to the NEPD mixture and subjected to azeotropic distillation until the nonane and water are separated. The resulting NEPD-butanol mixture is then allowed to cool whereupon NEPD crystallizes in high yield.

EXAMPLE 5

The experiment of Example 4 is repeated in all essential details except that an aqueous solution of 2-nitromethylpropanol (NMP) is mixed with suitable amounts of n-butanol and butyl ether. Crystalline NMP is obtained in good quality and high yields.

EXAMPLE 6

The experiment of Example 4 is repeated in all essential details except that an aqueous solution of 2-nitro-2-methylpropanediol (NMPD) is substituted for NEPD and n-butyl acetate is substituted for nonane in appropriate amounts. Crystalline NMPD is obtained in good quality and high yield.

I claim:

1. A process for the separation of nitroalkanol from an aqueous solution thereof, comprising the steps of (a) adding thereto an organic liquid mixture consisting essentially of an aliphatic alcohol of 2-4 carbon atoms and a hydrocarbon of 6-9 carbon atoms, said organic liquid mixture added to the aqueous solution in an amout in excess of that required to form a ternary azeotrope with water, (b) separating the water as a vapor by azeotropic distillation at least until crystals appear in the unvaporized portion of the mixture, (c) cooling the unvaporized portion of the mixture thereby causing substantially complete separation of the nitroalkanol, and (d) recovering the nitroalkanol from the unvaporized mixture.

2. The process of claim 1 wherein the hydrocarbon is benzene or toluene.

3. The process of claim 1 wherein the hydrocarbon is an alkane.

4. The process of claim 3 wherein the alkane is hexane.

5. The process of claim 3 wherein the alkane is heptane.

6. The process of claim 3 wherein the alkane is octane.

7. The process of claim 3 wherein the alkane is nonane.

8. The process of claim 1 wherein the nitroalkanol is 2-nitro-2-methylpropanol.

9. The process of claim 1 wherein the nitroalkanol is 2-nitro-2-methylpropanediol.

10. The process of claim 1 wherein the nitroalkanol is 2-nitro-2-ethylpropanediol.

11. The process of claim 1 wherein the nitroalkanol is tris(hydroxymethyl)nitromethane.

12. The process of claim 1 wherein the alkanol is ethanol.

13. The process of claim 1 wherein the alknaol is propanol.

14. The process of claim 1 wherein the aliphatic alcohol is butanol.

15. A process for the separation of nitroalkanol from an aqueous solution thereof comprising the steps of (a) adding to the solution an organic liquid mixture consisting essentially of two components which form a ternary azeotrope with water, one of the components being a poor solvent for the nitroalkanol, (b) subjecting the resultant mixture to azeotropic distillation to separate at least a major portion of the water, (c) cooling the unvaporized portion of mixture, thereby causing substantially complete separation of the nitroalkanol and (d) recovering the nitroalkanol from the unvaporized portion of the mixture.

16. The process of claim 15 wherein the organic liquid consists of an aliphatic alcohol of 2-4 carbon atoms and a second liquid selected from the group consisting of an aromatic liquid of 6-8 carbon atoms, an alkane of 6-9 carbona atoms, a ketone of 4-6 carbon atoms, propyl acetate, butyl acetate, butyl formate, or butyl ether.

17. The process of claim 15 wherein the organic liquid consists of n-propanol and n-propyl acetate.

18. The process of claim 15 wherein the organic liquid consists of n-propanol and 2-hexanone.

19. The process of claim 15 wherein the organic liquid consists of n-butanol and n-butyl acetate.

20. The process of claim 15 wherein the organic liquid consists of n-butanol and butyl ether.

21. The process of claim 15 wherein the organic liquid consists of iso-butanol and isobutyl acetate.

22. The process of claim 15 wherein the organic liquid consists of n-butanol and n-butyl formate.

23. The process of claim 15 wherein the organic liquid consists of iso-butanol and isobutyl formate.

* * * * *

UNITED STATES PATENT AND TRADEMARK OFFICE
CERTIFICATE OF CORRECTION

PATENT NO. : 4,416,734

DATED : November 22, 1983

INVENTOR(S) : Jacobs

It is certified that error appears in the above-identified patent and that said Letters Patent is hereby corrected as shown below:

Column 1, line 38 --200 g-- should read "220 g"

Claim 1, line 21 --amout-- should be "amount"

Claim 15, line 20, after --water--, add "as a vapor,"

Claim 16, line 29, "carbona" should read -- carbon --.

Signed and Sealed this

Sixth Day of November 1984

[SEAL]

Attest:

GERALD J. MOSSINGHOFF

Attesting Officer

Commissioner of Patents and Trademarks